United States Patent [19]

Gibson et al.

[11] Patent Number: 5,548,217
[45] Date of Patent: Aug. 20, 1996

[54] MICROWAVE SPECTROMETERS

[76] Inventors: Colin Gibson, 2 Agincourt Road, Penylan, Cardiff, CF2 5BN; Ian P. Matthews, 1, Linden Avenue, Penylan, Cardiff, CF2 5HG; Alan H. Samuel, 22 Foreland Road, Whitchurch, Cardiff, CF4 7AR; Zhangwhu Zhu, 50, Plantagenet Street, Riveside, Cardiff, CF1 8RP, all of United Kingdom

[21] Appl. No.: 441,060

[22] Filed: May 15, 1995

Related U.S. Application Data

[63] Continuation of Ser. No. 613, Jan. 5, 1993, abandoned, which is a continuation-in-part of Ser. No. 662,325, Feb. 25, 1991, Pat. No. 5,209,902, which is a continuation of Ser. No. 893,544, Jul. 7, 1986, abandoned.

[30] Foreign Application Priority Data

Nov. 10, 1984 [GB] United Kingdom .................. 8428470
Nov. 8, 1985 [WO] WIPO ..................... PCT/GB85/00509

[51] Int. Cl.$^6$ .............................................. G01R 33/20
[52] U.S. Cl. ........................ 324/316; 324/314; 324/313; 324/636
[58] Field of Search ................................. 324/316, 314, 324/313, 636, 634

[56] References Cited

U.S. PATENT DOCUMENTS

| | | | |
|---|---|---|---|
| 3,197,692 | 7/1965 | Hyde | 324/316 |
| 3,348,136 | 10/1967 | Nelson | 324/317 |
| 3,350,633 | 10/1967 | Hyde | 324/317 |
| 3,372,331 | 3/1968 | Larson | 324/317 |
| 3,585,494 | 6/1971 | Bozanic | 324/317 |
| 3,691,453 | 9/1972 | Rupp | 324/317 |
| 3,691,454 | 9/1972 | Hrubesh | 324/317 |
| 4,593,248 | 6/1986 | Hyde | 324/317 |

FOREIGN PATENT DOCUMENTS

62309/90 12/1990 Australia.

OTHER PUBLICATIONS

Ogasawara: "Highly Sensitive Procedures for Measuring Permeabilities for Circularly . . . "—IEEE Trans. on Magnetics—May 76—pp. 256–259.
By W. Fehse et al., "The Construction of a Microcomputer Controlled Microwave–Microwave Double Resonance Spectrometer Incorporating Two Crossed Fabry–Perot Resonators", May 1983, pp. 263–270, vol. 97, The Netherlands.
By W. Kolbe et al., "GHz pulsed Fourier transform microwave spectrometer", Jan. 1985, pp. 97–102, vol. 56, No. 1.
By A. Dymanus, "High–Q Stark Cavity Absorption Cell for Microwave Spectrometers", Mar. 1959, vol. 30, Nov. 3, pp. 191 –195.
By L. Hrubesh et al., "A Gunn Diode Microwave Cavity Spectrometer", Jun. 1969, pp. 595–560.
By R. Collier, "Variable–Frequency Microwave Cavity Spectrometer", Dec. 1954, vol. 25, No. 12, pp. 1205–1207.
B. W. Kolbe et al., "140 GHz Microwave Spectrometer for the Detection of Gaseous Chemical Species", Nov. 1983, pp. 733–749.
By G. Reesor et al., "X–band Spectrometer with a Rectangular Resonant Stark Cell", Jun. 1975, vol. 46, No. 6.

(List continued on next page.)

*Primary Examiner*—Kenneth A. Wieder
*Assistant Examiner*—Jose M. Solis
*Attorney, Agent, or Firm*—Young & Thompson

[57] ABSTRACT

A microwave spectrometer includes a sensing chamber into which is introduced a gas or constituent to be analyzed. Microwave radiation is introduced into the chamber and any of the chamber resonant frequency, the microwave frequency, and the center frequency of the absorption peak are varied independently. The resultant variation in intensity of the microwave radiation in the chamber is monitored to determine the concentration of the gas within said chamber. The spectrometer may include a frequency measuring and reference system for measuring the resonant frequency of the chamber.

7 Claims, 12 Drawing Sheets

OTHER PUBLICATIONS

By R. Nandi et al., "Microwave–microwave double resonance using a Fabry–Perot cavity spectrometer", Oct. 1983, vol. 54, No. 10, pp. 1377–1379.

By H. Uehara et al., "Continuous Ammonia monitor using a Stark microwave cavity resonator onator", Mar. 1980, vol. 51, No. 3, pp. 334–337.

By M. Lee et al., "A Cavity Type Absorption Cell for Double Resonance Microwave Spectrosccopy", Apr. 1972, vol. 43, No. 4, pp. 638–640.

By H. Uehara et al., "A Sensitive Microwave Cavity Spectrometer: Direct Detection of Formaldehyde in Automobile Exhaust", Oct. 15, 1974, vol. 28, No. 4, pp. 597–599.

By L. Hrubesh et al., "A Cavity Search Spectrometer for Free Radical Microwave Rotational Absorption Studies", Jun. 1971, vol. 42, No. 6, pp. 789–796.

a) GUNN DIODE CONTROL VOLTAGE b) PIEZOELETRIC CONTROL VOLTAGE

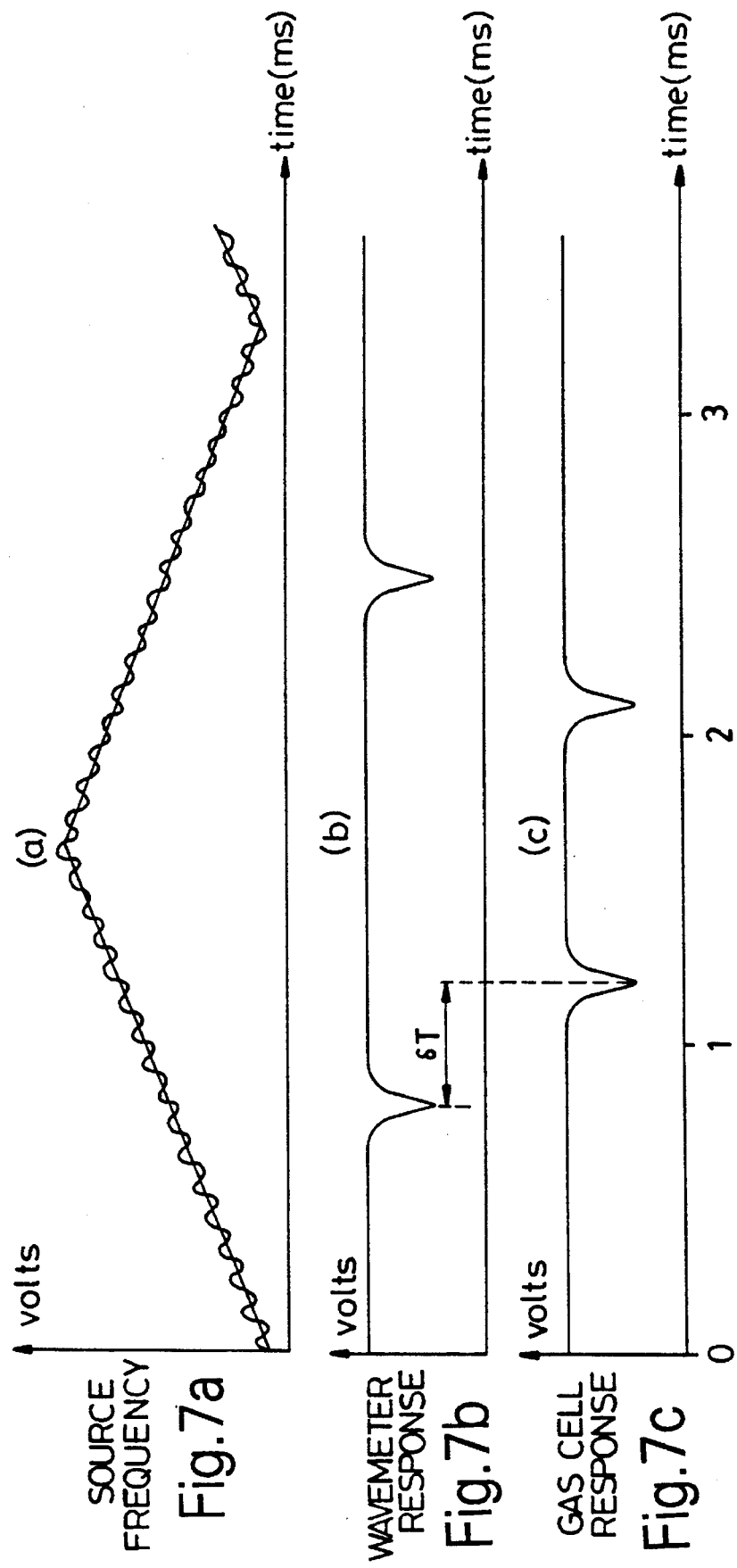

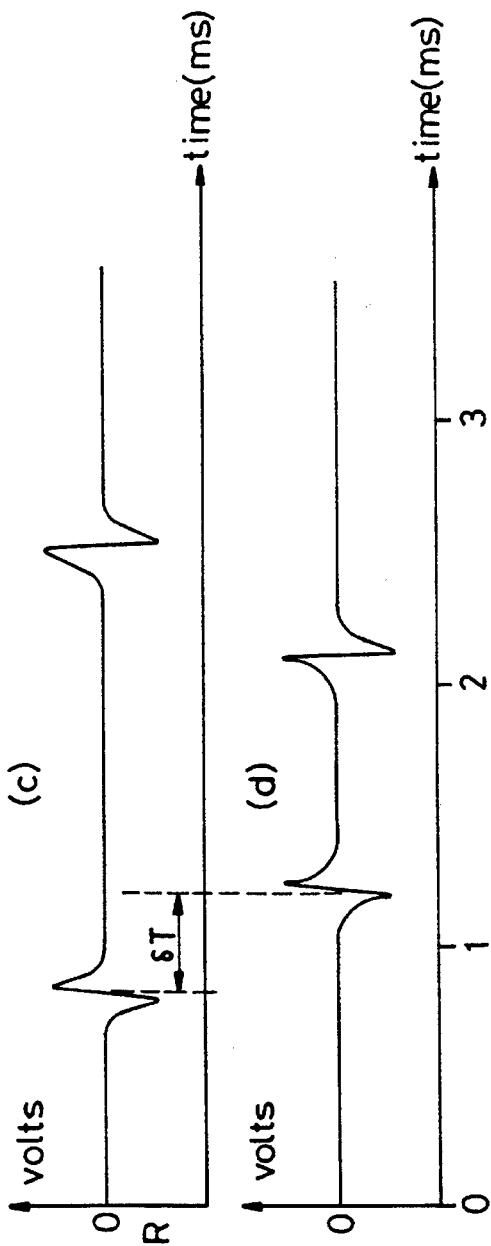
Fig.8a DITHER FROM WAVEMETER
Fig.8b DITHER FROM GAS CELL
Fig.8c PHASE SIGNAL FROM WAVEMETER
Fig.8d PHASE SIGNAL FROM GAS CELL

MICROWAVE SPECTROMETERS

This application is a continuation of application Ser. No. 08/000,613, filed Jan. 5, 1993, now abandoned, which is a continuation-in-part of application Ser. No. 07/662,325 filed Feb. 25, 1991, now U.S. Pat. No. 5,209,902 which is a continuation of application Ser. No. 06/893,544 filed Jul. 7, 1986, now abandoned.

This invention relates to apparatus and methods for detecting the presence or concentration level of a gas or constituent.

Molecular rotational microwave spectrometer is a fundamental analytical technique. Operating on the principle of quantised absorption of electromagnetic radiation, a molecular dipole in the gas phase will exhibit promotion of its rotational state to one of many available energy levels resulting in a highly characteristic narrow bandwidth (absorption) spectrum unique to that molecular species, reflecting as it does properties of the entire molecule rather than those of just the nucleus or constituent atoms or groups. Furthermore the magnitude of absorption maxima at resonant frequencies is related to the molecular concentration of the analyte and at low pressures when molecular interactions are at a minimum a linear concentration relationship is established. Absorption "peaks" for many compounds may be detected at frequencies in the microwave range.

In the past, microwave spectrometers have been designed and built but have not been successful commercially. It is thought that a major reason for this is the complexity associated with their frequency synchronisation, reference, stabilization and measurement systems. In one earlier device utilising a non-resonant gas cell, the microwave radiation source is a backward wave oscillator (BWO) frequency stabilized by phase locking its output to a harmonic of a 400 to 420 MHz reference oscillator. The frequency sweeping is made by varying the reference oscillator and thereafter adjusting the "slaved" BWO frequency by the phase lock system. The frequency reference system, and the "slaved" BWO system are technically feasible but costly. In another earlier device also utilising a non-resonant gas cell, instead of phase locking the radiation source to a reference oscillator, a simple free-sweeping BWO radiation source is used together with a complicated frequency measurement (marker) system. In this system, the fundamental frequency standard is a crystal controlled 1 MHz oscillator which is locked to 1 MHz, 10 MHz, 100 MHz and 1 GHz local oscillators. These local oscillators act as frequency references in a series of frequency marking stages and compare with the source frequency, giving an appropriate marker at each stage.

Current proposals employing a resonant cavity gas cell seek to either phase-lock the source frequency to the resonant frequency of cavity gas cell, or phase-lock the resonant frequency of the cavity gas cell to the centre frequency of the molecular absorption peak, or phase-lock the source frequency to both the resonant frequency of the cavity gas cell and the centre frequency of the molecular absorption peak. However, in the first case, the cavity gas cell is in fact not a stable frequency reference, since the resonant frequency may be affected by various factors, for example, mechanical rigidity, dielectric constant of the gas sample and pressure. In the second case this may be theoretical but not practical. In the third case, the signal to drive the phase-locking loop relies upon the strength of the absorption signal of the analyte gas and would in fact become lost in the background noise since the absorption signal is usually very small and requires a large time constant lock-in detection system to recover from the background noise.

Accordingly, in one aspect, this invention provides apparatus for sensing or measuring a gas or constituent, comprising:

a chamber into which the gas or constituent is introduced;

means for propagating microwave radiation into said chamber;

chamber resonant frequency adjustment means for varying the resonant frequency of said chamber;

source frequency adjustment means for varying the frequency of said microwave radiation;

detector means for detecting said microwave radiation in said chamber, and processor means for controlling said chamber frequency adjustment means and said source frequency adjustment means and for responding to the output of said detector means to determine at least one of the presence of concentration level of said gas or constituent.

Preferably said control means controls said chamber resonant frequency adjustment means and said source frequency adjustment means so that a multiple sequential scanning modulation is applied to at least one of said microwave frequency and said chamber resonant frequency thereby to enhance the signal detected by said detector means. Said multiple sequential scanning may comprise adjusting one of the chamber resonant frequency and said source frequency stepwise and, at each step, performing at least one sweep of the other thereof, whereby said chamber resonant frequency and said source frequency vary independently to coincide or match at least once during each step.

The chamber resonant frequency adjustment means may comprise means for varying at least one parameter of the chamber, for example at least one dimension of the chamber. The means for varying may comprise a drive means such as a piezoelectric transducer for moving a member or wall element.

Alternatively, said drive means may comprise rotary drive means for rotating a wall element closing an aperture in said chamber, the surface of said wall element facing the chamber being formed so that on rotation thereof the dimensions of the chamber are varied. Here, the surface of said wall element facing the chamber may be a generally flat surface with at least one depression formed therein whereby, on rotation of said wall element, the aperture is alternately closed by said flat surface and said depression, thereby varying at least one dimension of the chamber between at least two values.

In another aspect said means for varying may comprise means such as a varactor diode for varying the impedance of the chamber.

The apparation may include absorption peak frequency adjustment means for adjusting at least one of the frequency and amplitude of the absorption peak of the gas or constituent being sensed or measured. The absorption peak frequency adjustment means may comprise means for exposing the gas or constituent to a varying electric or magnetic field thereby to shift the absorption peak.

The apparatus may include a pumping source of energy in which case said absorption peak frequency adjustment means may comprise means for adjusting the amplitude of the pumping source.

Where the frequency of the microwave radiation propagated in the apparatus varies with time, the apparatus may include frequency reference means for determining the resonant frequency of the chamber, said frequency reference means comprising means for passing a component of said microwave radiation from said propagating means to a reference cavity means having a predetermined resonant frequency, reference detector means for detecting the intensity of said component of microwave radiation in said reference cavity means, means responsive to the relative timings and/or phases of the outputs of said chamber detector means and said detector means to output a signal representative of the resonant frequency of the chamber. Said reference cavity means may be adjustable to allow the resonant frequency thereof to be adjusted.

Said processor means may directing or indirectly monitor the curve represented by the variation of absorption coefficient of the gas or constituent with frequency and determines the concentration level of said gas or constituent based upon the area of the curve under the absorption peak associated with said gas or constituent.

In a further aspect, this invention comprises apparatus for sensing or measuring a gas or constituent, comprising:

a chamber into which the gas or constituent is introduced;

means for propagating microwave radiation into said chamber;

means for varying at least two of the following parameters of the apparatus independently:
(a) the resonant frequency of the chamber;
(b) the frequency of the microwave radiation; and
(c) the frequency of a selected absorption peak in the absorption coefficient v.s. frequency characteristic of said gas or constituent, detector means for detecting the microwave radiation within said chamber, and processor means responsive to the output of said detector means and to the variations in said parameters to determine at least one of the presence or concentration level of said gas or constituent of the spectrometer.

The advantages of this technique are that the difficulties experienced in earlier known spectrometers with locking, say, the source frequency to the cavity resonance frequency or the cavity resonant frequency to the centre frequency of the absorption peak etc. may be obviated. Also, this technique greatly increases the flexibility of the instrument since a variety of modulation techniques may be applied to each parameter unilaterally and without the need to consider the implications for any of the others. For example, to improve the signal to noise ratio of the measurement, source modulation may be applied at a relatively high frequency even though cavity and absorption peak modulation may be limited by practical considerations to relatively low frequencies. Thus, as a result, a single instrument may operate in real time over a wide range of frequencies thus enabling several gases to be measured simultaneously whilst in mixture of many gases.

There are a number of techniques already in existence, in order to vary parameters (a) to (c) noted above. For example, (a) The centre frequency of the absorption peak may be varied by means of the Stark effect or the Zeeman effect, i.e. through the application of an electric or magnetic field.

(b) The resonant frequency of the cavity may be varied through manipulation of the cavity dimensions or by variations in cavity impedance as may be achieved using a varactor diode.

(c) The source frequency may be varied by a number of techniques some of which would be incorporated into a variable frequency Gunn oscillator.

The relevant concentration information may be extracted in a number of ways depending upon the performance requirements of the spectrometer. Briefly, the effect of independent or asynchronous modulation of the aforementioned parameters is to result in a complex signal output from the cavity which contains a frequency component or components, the magnitude(s) of which is (are) related to the analyte gas concentration. More specifically, the output signal from the cavity is amplitude modulated by the presence of the gas. This amplitude modulated signal may be demodulated in a number of ways, for example by using an envelope detection system similar to that described previously.

Said means for varying preferably applies a frequency modulation to at least one of said parameters and this may comprise a double frequency modulation comprising a relatively low frequency modulation and a relatively high frequency modulation.

The processor means preferably includes means for demodulating the output of said detector means thereby to determine at least one of the presence or concentration level of said gas or constituent and said means for demodulating may include means for mixing the output of said detector means with a reference signal corresponding to said frequency modulation.

Said chamber may be a resonant cavity or it may comprise a non-resonant cavity coupled to tunable bandpass filter means, wherein said detector means detector the radiation transmitted by said filter means. Here the centre line of the filter means is analogous to the resonant frequency of the resonant cavity.

Said processing means preferably determines the absolute concentration level of said gas or constituent based upon the area of an absorption peak corresponding to said gas or constituent in the absorption coefficient v.s. frequency characteristics thereof or that part of the area swept during use.

Said means for varying may vary the resonant frequency of the chamber and the frequency of the microwave radiation independently with respect to each other or it may vary the frequency of said selected absorption peak and the frequency of the microwave radiation and the latter option may be preferable in many applications to minimise baseline distortion.

Where a gas or constituent with little or no permanent dipole moment is to be sensed or measured, the apparatus may comprise dipole inducing means for inducing in said gas or constituent a momentary dipole moment. Said dipole inducing means may comprise means for exposing said gas or constituent to electromagnetic radiation to induce momentary dipole moments therein, and means for applying an electric field thereto. Said means for exposing may generate infra-red visible light or ultraviolet radiation.

Alternatively, said dipole inducing means may include means for ionizing the gas or constituent, and said ionizing means may comprise means for exposing the gas or constituent to ionizing radiation or means for introducing or mixing into said gas or constituent a substance from a relatively strong polar molecular species.

In a further aspect of this invention there is provided a microwave spectrometer including a chamber into which a gas or constituent is introduced and means for propagating microwave radiation in or into said chamber, a frequency reference means for determining the resonant frequency of said chamber means, said frequence reference means comprising means for passing a component of said microwave radiation from said propagating means to a reference cavity means having a predetermined resonant frequency, reference detector means for detecting the intensity of said component of microwave radiation in said reference cavity means, chamber detector means for detecting the intensity of said microwave radiation in said chamber means and processor means responsive to the relative timings and/or phases of the outputs of said chamber detector means and said reference detector means to output a signal representative of the resonant frequency of the chamber.

In yet another aspect of this invention there is provided a method for sensing or measuring a gas or constituent, which comprises the steps of:

(i) introducing the gas or constituent into a chamber, (ii) exposing the gas or constituent to microwave radiation, (iii) independently varying at least two of the following parameters:
  (a) the frequency of said microwave radiation;
  (b) the resonant frequency of said chamber;
  (c) the frequency of the absorption peak, and (iv) monitoring within or outside said chamber the variation of the intensity of the microwave radiation in said chamber in relation to said independent variation, thereby to determine at least one of the presence and concentration level of said gas or constituent.

In another aspect, this invention provides apparatus for sensing or measuring a gas or constituent comprising a chamber into which the gas is introduced and characterised by means for propagating radiation in or into the chamber and means for tuning the cavity afforded by the chamber.

Preferred embodiment of the invention described herein implement a novel and simple frequency reference and measurement system in a microwave cavity spectrometer which has a free sweeping radiation source, a free tuning resonant cavity gas cell and a free setting cavity wavemeter frequency reference, thus obviating the requirement for any phase locking systems for frequency reference, stabilization and measurement.

BRIEF DESCRIPTION OF THE DRAWINGS

The invention may be performed in various ways and certain specific embodiments with different signal treatment systems will now be described by way of example with reference to the accompanying drawings, in which:

FIGS. 7(a), 7(b), and 7(c) are time diagrams for the frequency reference and measurement system of FIG. 5, showing (a) the sweeping signal applied to the microwave source, (b) the signal from the cavity wavemeter and (c) the signal from the cavity gas cell;

FIGS. 8(a) to 8(d) are time diagrams for the system of FIG. 6, showing (a) the dither signal from the cavity wavemeter, (b) the dither signal from the cavity gas cell and (c) and (d) the signals from the phase sensitive detectors for the cavity wavemeter and the cavity gas cell respectively;

DETAILED DESCRIPTION OF THE INVENTION

Figure 1:
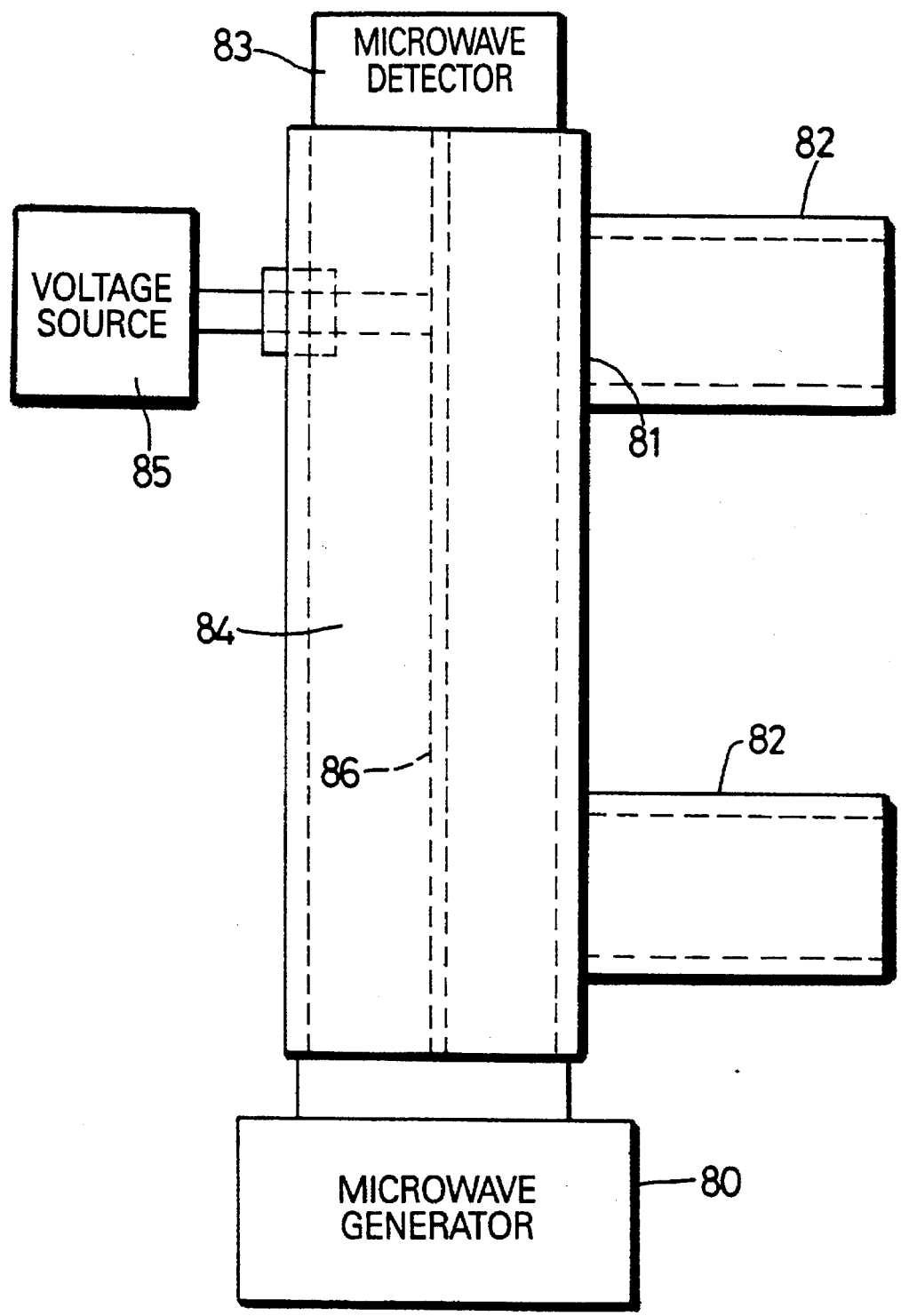
FIG. 1 is a diagram illustrating a first embodiment of microwave spectrometer.

FIG. 1 illustrates a microwave molecular rotational spectrometer for detecting the presence and concentration level of Ethylene Oxide and other gases and is comprised of a rectangular wave guide tube 81 having a Klystron, Gunn diode or other suitable microwave generator 80 at the lower end and one or more microwave detectors 83 at the upper end. the interior of the tube is connected to and communicates with the exterior of the tube via two branch tubes 82 each equipped with a microwave choke to prevent the escape of microwave energy while permitting the free diffusion of gases and vapours to be analysed via suitable permeable septa, semi-permeable septa, or valve arrangements. Within the tube 81 is a thin insulated metal strip electrode 86 positioned centrally along the major axis of the tube. This electrode is connected to an external alternating square wave voltage source 85 such that a potential difference arises between the electrode and the tube during every half of the alternating voltage cycle giving rise to "Stark" splitting of the angular momentum of the molecular dipoles and a corresponding shift in the frequency of the microwave absorption for the particular molecular rotational transition under observation. The microwave detector passes signals to a detector amplifier which incorporates a phase sensitive discriminator operating synchronously with the "Stark" modulated voltage. The detector amplifier output thus reflects microwave energy absorption occurring each half cycle during zero electrode potential. This arrangement improves sensitivity by improving the signal to noise ratio.

According to another preferred feature where greater spectrometer sensitivity is required the waveguide tube 81 may be replaced by a micro-wave resonant cavity of high quality (Q) factor connected to and communicating with the exterior of the cavity as previously described and having a microwave generator and one or more microwave detectors at appropriate positions and a central electrode with which to employ the "Stark" effect.

The pressure of the gas sample in the spectrometer is approximately 20 millitorr maintained by a high vacuum pump. Gas molecules diffuse into the spectrometer through permeable septa, semi-permeable septa or valve arrangements.

Figure 2:
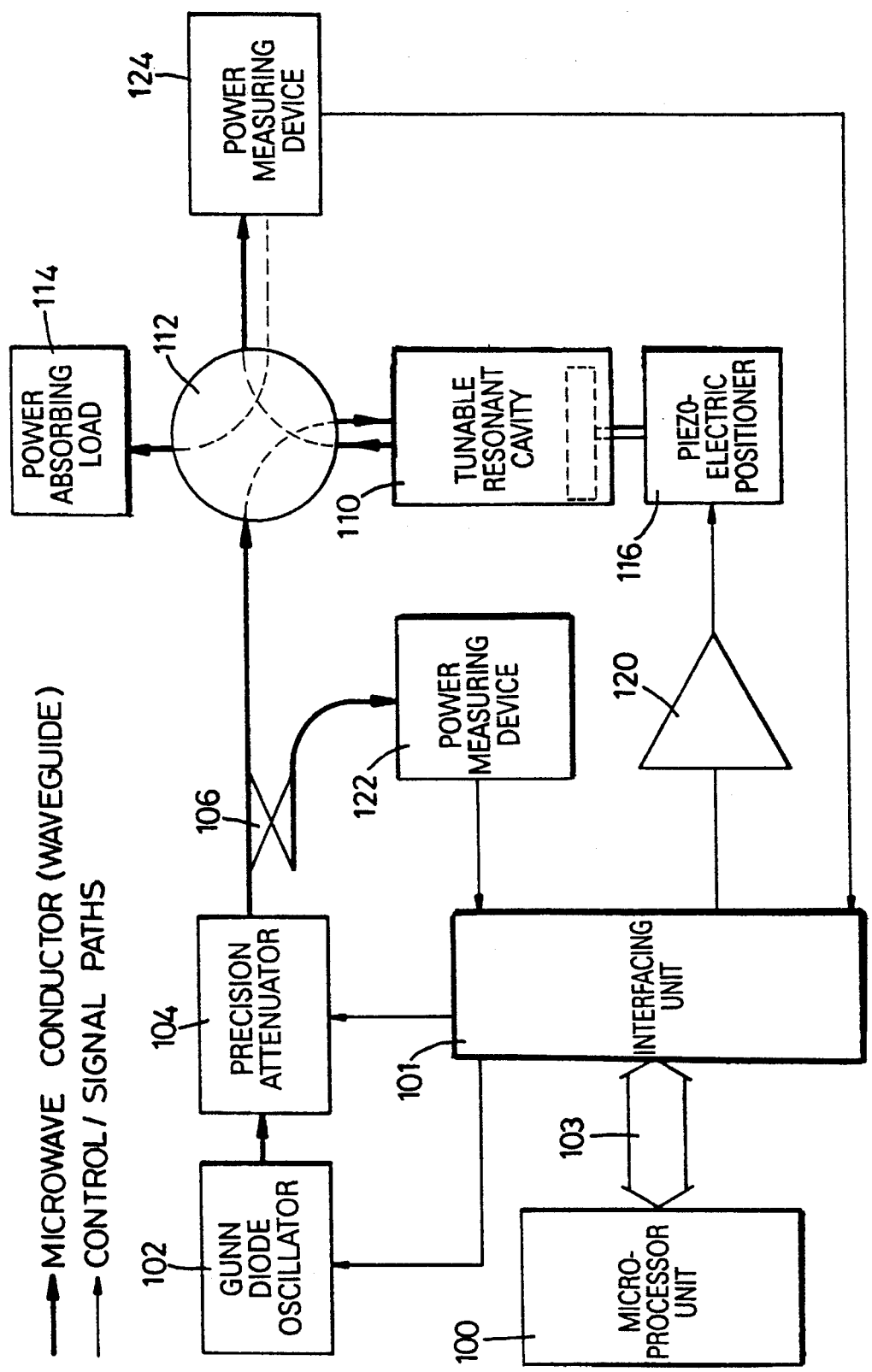
FIG. 2 is a diagram illustrating components of a second embodiment of microwave spectrometer.

According to yet another preferred feature a microwave rotational spectrometer utilising multiple sequential scanning as a means of signal enhancement which obviates the need for "Stark" modulation voltages may be used. FIG. 2 is a schematic diagram of such a spectrometer control. In this system a microprocessor unit 100 is arranged to control automatically the operation of the instrument and analyse the data received from the power measuring devices. An interfacing unit 101 includes electronic circuitry to link the microprocessor data bus 103 to the remainder of the spectrometer components. A variable frequency microwave source such as a Gunn Diode Oscillator 102, under the control of the microprocessor is arranged to "search" for a specific absorption peak by sweeping a preselected frequency band. The power output from the oscillator is limited by means of a precision attenuator 104. A directive coupling 106 splits the microwave beam from the Gunn Oscillator into two parts so that the power incident upon the gas filled cavity 109 may be continuously monitored by sensing one part of the beam. A waveguide circulator 112 enables the other part of the microwave beam to be fed into/out of the same cavity orifice. This avoids the possibility of interference between the incident and transmitted beams which would adversely affect the accuracy of measurement. A power absorbing load 114 soaks up any microwave power reflected from the measuring devices.

The tunable resonant cavity 110 has its resonant frequency varied electromechanically in order to match it to the frequency of the input radiation periodically or episodically when either the frequency of the input radiation or the resonant frequency of the cavity or both are modulated as a means of signal enhancement. This would enable the use, for example, of phase sensitive detection techniques without the need to use a "Stark" modulated voltage. As a result, at resonance the microwave beam will pass through the comparatively small volume of gas very many times, thus greatly increasing the efficiency of the absorption.

The necessary minute changes in cavity geometry are achieved with the desired degree of precision by means of a piezoelectric positioning device 116. This converts changes in an applied voltage into changes in mechanical displacement. The device 116 is powered by an amplifier 120 controlled from the microprocessor interfacing unit 101, and there are two power measuring devices 122, 124 also associated with the interfacing.

Figure 3:
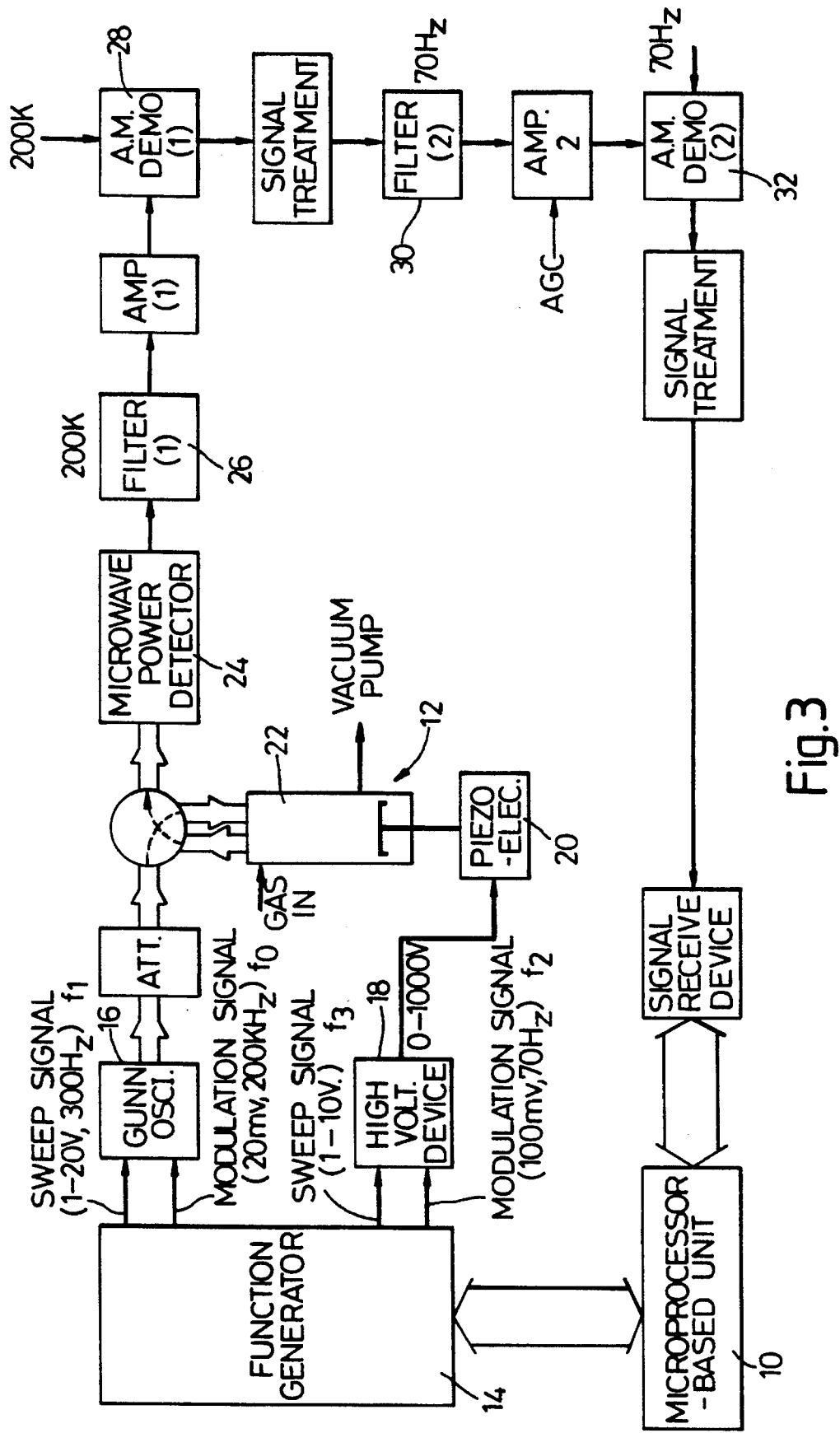
FIG. 3 is a schematic diagram of a signal treatment system for the embodiments of FIGS. 1 and 2 utilising cavity modulation in the cavity gas cell coupled with asynchronous source modulation.

Referring now to FIG. 3 the basic components of the spectrometer are similar to those in the first and second embodiments and will not be described again. A microprocessor 10 controls operation of the overall system and analyses the signals received from the gas sensor 12. A function generator 14, under the control of the microprocessor 10 generates sweep signals and modulation signals for a voltage-controlled Gunn oscillator 16 and a high voltage driver 18 for a piezoelectric positioning device 20. Gas to be sensed is introduced into a sensing cavity 22 and the frequency of the incoming radiation and the resonant frequency of the cavity 22 are adjusted by the Gunn oscillator 16 and the piezoelectric positioning device 20.

The voltage controlled Gunn oscillator or diode 16 is controlled chiefly by a sweep signal (typically 1–20 V, 300 Hz [$f_1$]) which searches for the resonant frequencies of the cavity 22 of the gas sensor 12. A small modulation "dither" voltage signal (typically 200 KHz[$f_o$]) is superimposed by the function generator on the sweep signal and so a microwave FM signal is obtained in the waveguide. The FM signal passes through the cavity and will then be transformed into a 200 KHz AM signal by the microwave power detector 24 which is proportional to the differential of the frequency characteristic of the cavity.

The tunable resonant cavity 22 of the gas sensor 12 will have its resonant frequencies altered electromechanically. This will be achieved by means of a piezoelectric positioning device, enabling the length of cavity to be alterable. A sweep signal (typically 0–10 v, about one Hertz [$f_3$]) is used to search for the gas absorption line on which is a small voltage signal (typically 100 mV, 70 Hz [$f_2$]) superimposed, thus an AM signal of 70 Hz is obtained, which is proportional to the differential of the absorption line.

A first filter 26 will allow the frequency components around $f_o=200$ KHz (thus fo, fo±$f_1$, fo±$f_2$, $f_o$–±($f_2$±$f_3$), fo±$f_3$) to pass, and through a first demodulator 28, the signals of frequency components $f_1$, $f_2$, $f_3$, $f_2$±$f_3$ will remain. A second filter 30 will allow the components around $f_2=70$ Hz (thus, only $f_2$, $f_2$±$f_3$) to pass and through a second demodulator 32, only signal of $f_3$ (i.e. the differential of absorption line) will remain.

Through a first amplifier AMP(1), a signal with absorption coefficient $10^{-5}$ cm$^{-1}$ (i.e. 10% of skin effect) can be easily detected. Using a second AGC (Automatic gain control) amplifier AMP(2), an AMP(2) with a gain of 10 may be used to amplify a signal of $10^{-6}$ cm$^{-1}$, an AMP(2) with a gain of $10^2$ may be used to amplify a signal of $10^{-7}$ cm$^{-1}$, and an AMP(2), with a gain of $10^n$ may be used to amplify a signal of $10^{-5-n}$ cm$^{-1}$. It should be noted that the absorption coefficient of EO is $10^{-5}$ cm$^{-1}$ i.e. with 100% concentration.

Figure 4A:
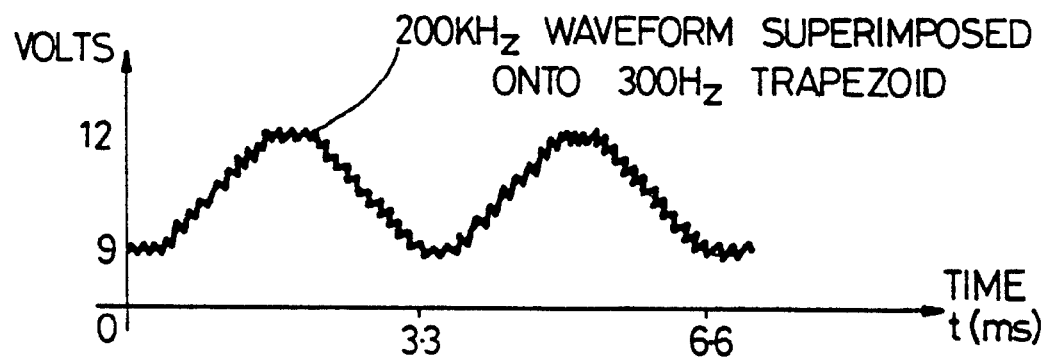
FIGS. 4(a) and 4(b) are diagrams illustrating the modulation waveforms applied in the signal treatment system of FIG. 3.

In use the centre frequency of the Gunn oscillator 16 and the centre frequency of the resonant cavity 22 are set to correspond to one of the absorption peaks of the gas or constituent under observation. These frequencies are modulated as described above and typical control voltage waveforms for the Gunn oscillator 16 and the piezoelectric positioning device 20 are shown in FIGS. 4(a) and (b) respectively. Both of these voltage waveforms are transformed into frequency variations by each device to provide frequency modulation of the source frequency (i.e. source modulation) and the resonant frequency of the cavity (i.e. cavity modulation)

Figure 4B:
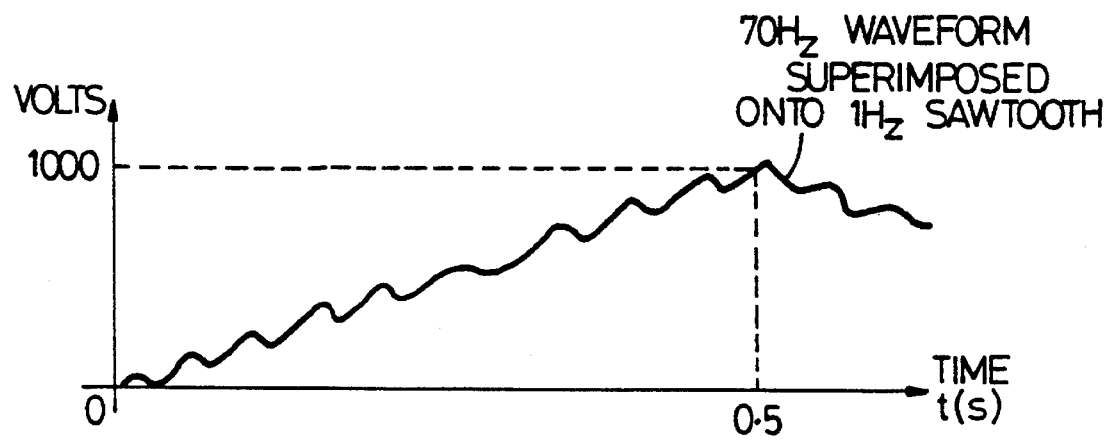

As is evident from FIGS. 4(a) and 4(b) although it is possible for the frequency of the source and the resonant frequency of the cavity to coincide, most of the time they will not coincide (in other words, cavity modulation coupled with asynchronous source modulation).

This being the case, the detector will pick up a complex signal. However, the detected signal is structured such that there is a lot of useful information. In order to extract that information, the detected signal needs to be filtered ad processed. One such means of extracting the desired information is by means of a phase sensitive detection system. We use two separate "lock-in" amplifiers to pick out, firstly, the Gunn diode frequency modulation (200 KHz) and then, following rectification and filtering, a second "lock-in" amplifier to detect the resonant cavity modulation (70 Hz). The treated signal is then returned to the microprocessor via suitable interfacing and is proportional to the concentration of the gas under observation in the gas sensor 12.

The advantage of this set up is that a very high proportion of the noise (i.e. 1/f noise) present at detector is rejected, since the useful information (70 Hz) is carried by the dither carrier (200 Hz). This enables detection of very low power signals with the minimum of error, and without requiring either Stark or Zeeman modulation In yet another preferred feature, a microwave rotational spectrometer utilises multiple sequential scanning in the manner already described except that the frequency modulation of the microwave radiation incident upon the resonant cavity is either replaced by, or has added to it, amplitude modulation of that radiation.

Figure 5:
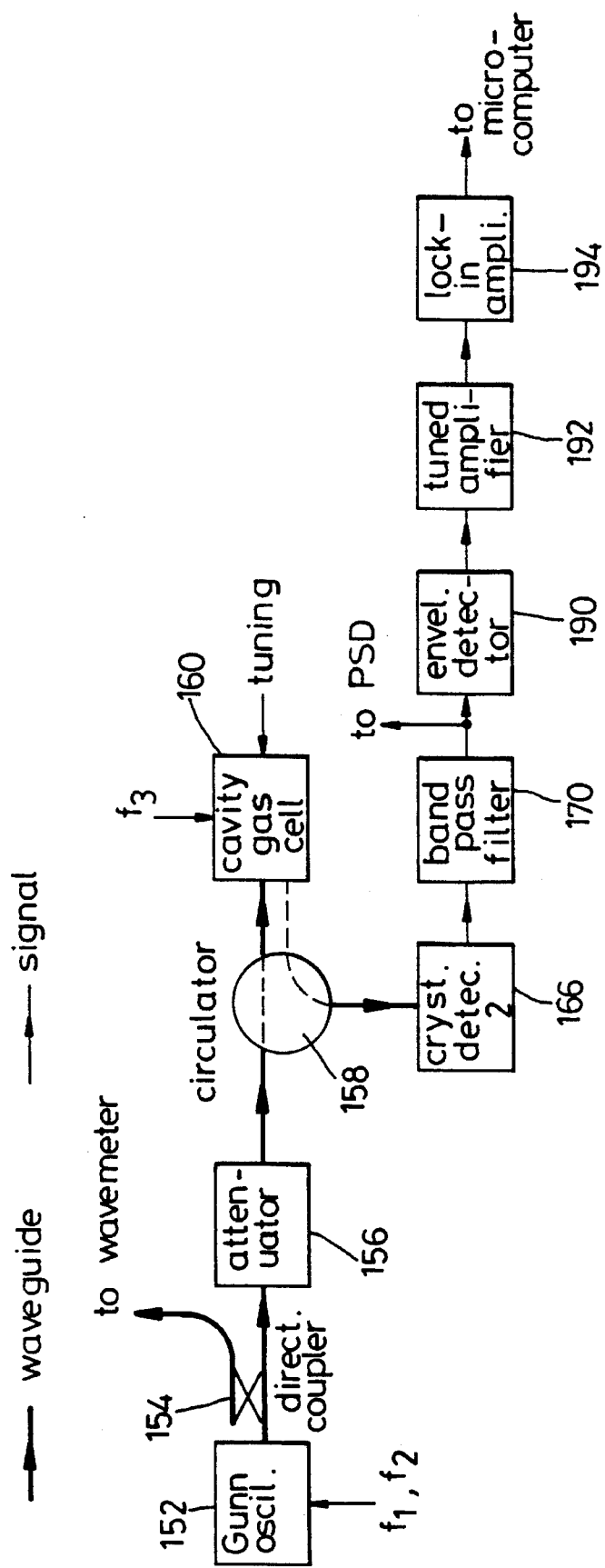
FIG. 5 is a schematic diagram of a signal treatment system for the embodiments of FIGS. 1 and 2, utilising either Start modulation, Zeeman modulation, double resonance or cavity modulation in the cavity gas cell combined with synchronous or independent source modulation.

Referring now to FIG. 5, there is illustrated a fourth embodiment of microwave spectrometer system which incorporates the frequency measurement system to be described below. The spectrometer comprises a microwave source 152 which feeds a microwave beam into a cavity gas call 160 via a directive coupler 154, an attenuator 156 and a circulator 158. The microwave source 152 is frequency-double-modulated by means of the sweeping signal (of frequency $f_1=300$ Hz) and the dither signal (of frequency $f_2=200$ kHz) (see the dotted line in FIG. 7(a), such that the microwave frequency is swept around the pre-selected cavity resonant frequencies of the gas cell and the wavemeter over a range of say $\pm 100$ MHz and so the resonant peaks of the gas cell and wavemeter appear in the tune domain to allow the resonant frequency of the gas cell to be determined as described previously.

At the same time a low frequency modulation such as Stark, Zeeman, double resonance or cavity modulation (of frequency $f_3$, say, 70 Hz) is applied in the cavity gas cell 160. The salient information of gas absorption arising from the $f_3$ modulation is carried by the $f_2$ dither signal. Having passed through the $f_2$ band pass filter 170, this salient information is then extracted by means of a series of dedmodulators and tuned amplifiers, including an envelope detector 190, a tuned amplifier 192 and a lock-in amplifier 194. The output is processed to determine the area bound by the curve defining the absorption peak of the gas or constituent being analysed.

An advantage of this technique is to furnish low frequency operation for modulation such as Stark, Zeeman, double resonance, or cavity modulation in the cavity gas cell whilst satisfying the criterion of achieving signal enhancement, i.e. the microwave crystal detector operates at relatively high frequency (i.e. approximately $f_2$, say, 200 kHz). This would reduce the cost of spectrometer system since a modulator (such as a high voltage generator for Stark modulation operating at relatively low frequency (say, several tens of kHz)) is much cheaper than that operating at relatively high frequency (say, several tens of kHz) as involved in coinventional microwave Stark spectrometers).

Figure 6:
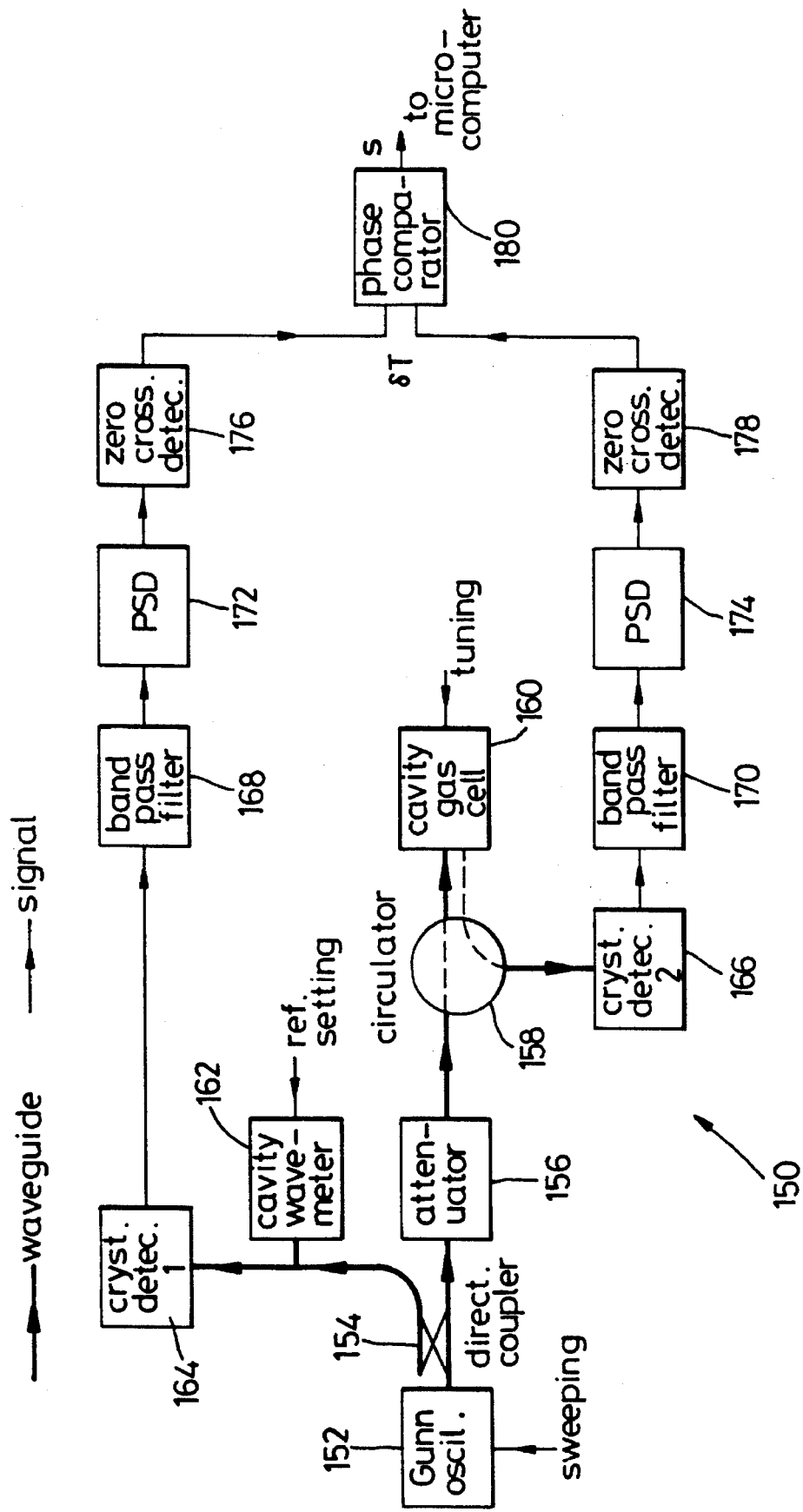
FIG. 6 is a diagram illustrating a frequency reference and measurement system in accordance with this invention.

Referring now to FIG. 6, the frequency reference and measurement system 150 for the microwave spectrometer uses the varactor-tuned Gunn oscillator 152 as a radiation source and the other half of the microwave beam exiting from the directive coupler 154 is fed into a cavity wavemeter 162 which is made of material with very small thermal coefficient and sealed with dry air and which acts as a frequency reference. As to be described below, the resonant frequency of the wavemeter may be adjusted for operational and calibration purposes. The Gunn oscillator 152 is frequency modulated by means of a sweeping signal (at frequency, $f_1$, say, 300 Hz), as shown in FIG. 7(a) by solid line, such that the microwave frequency of each beam is swept at $f_1$ around a pre-selected resonant frequency $F_r$ of the corresponding cavity over a range of, say, $\sim\pm 100$ MHz. As the microwave frequency passes back and forth through $F_r$, the microwaves are amplitude-modulated by the corresponding cavity resonant characteristic. Subsequently, the microwaves are transformed into respective electrical signals via crystal detectors 164 and 166, as shown in FIGS. 7(b) and (c). The phase difference $\delta T$ between the signals from the two crystal detectors can then be used to indicate the resonant frequency of the cavity gas cell 160 with reference to that of the cavity wavemeter 162.

In order to detect the phase difference $\delta T$, a relatively small magnitude/high-frequency ($f_2$, say, 200 kHz) "dither" signal is superimposed upon the sweeping signal, as shown in FIG. 7(a) by a dotted line. The signal from each crystal detector 164, 166 will contain frequency components around $f_2$. Through a bandpass filter 168, 170 of centre frequency $f_2$, the signal becomes an AM signal with a carrier frequency $f_2$, as shown in FIG. 8(a) or FIG. 8(b). Close to a cavity resonant frequency, the phase of the signal reverses, passing through zero phase at exactly the cavity resonant frequency. By using respective phase-sensitive-detectors (PSD) 172, 174 and zero-crossing detectors 176, 178 the zero phase (hence, the resonant frequency) is detected, as shown in FIGS. 7(c) or (d).

Figures 9A, 9B:
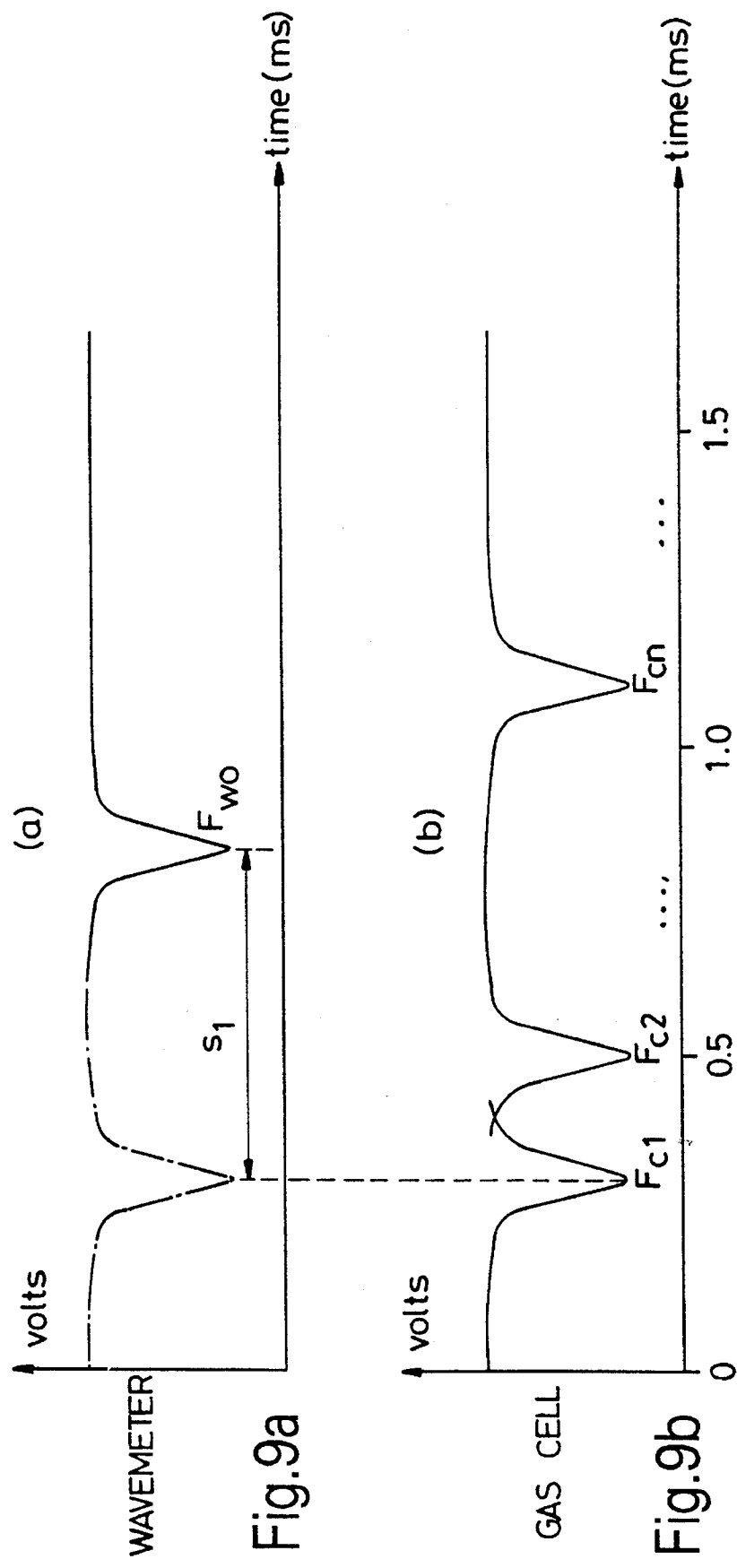
FIGS. 9(a) and 9(b) are oscilloscope time diagrams illustrating calibration of the system of FIG. 6.

A phase comparator 180 is used to derive a DC signal, s, which is proportional to $\delta T$. Finally, the DC signal is fed into a microcomputer for conversion to a frequency value. The system of FIG. 6 may be calibrated as follows, with reference to FIGS. 9(a) and (b). The initial cavity wavemeter resonant frequency $F_w$ is set to $F_{w0}$, say, 24.98 GHz, as shown in FIG. 9(a) by a solid line in the oscilloscope time diagram. The cavity gas cell resonant frequency $F_c$ is set to $F_c 1, F_c 2, \ldots, F_{cn}, \ldots$, as in FIG. 9(b), whilst, at each $F_c$ setting, the output signal, said $s_1$, from the phase comparator 180 is recorded. At each $F_c$ setting, $F_w$ is tuned close to $F_c$ setting, say $F_{c1}$, until s=0, as shown in FIG. 9(a) by a dotted liner and then recording $F_{c1}=F_{w1}$. Finally a calibration curve is generated by interpolating data set $\{F_{c1}, F_{c2}, \ldots\}$ against data set $\{s_1, s_2, \ldots\}$. It will be appreciated that the frequency measurement and reference system described above may be used in making frequency measurements other than for microwave spectrometry and this invention extends to such systems.

The frequency reference and measurement system described here is believed to be simpler than those employed in the spectrometer discussed earlier and more reliable than those of conventional cavity spectrometers. It should be noted that, in the above system the cavity gas cell is tuned free across a wide range over which the source sweeps with very little requirement for mechanical adjustments.

In general, the microwave spectrometer employing this frequency reference and measurement system has a radiation source which is swept free across a frequency range, a cavity gas cell which is tuned free across that range and a cavity wavemeter which resonant frequency is set free within that range. This would greatly improve its versatility since there is, theoretically, no limit to the frequency range over which the spectrometer system operates. Thus, it is possible to enable us to develop a microwave cavity spectrometer with a wide frequency range which may be capable of being a general purpose analytical spectrometer.

In the technique described above in connection with FIG. 9, we obtain various measurements, one of which may be the area under the curve representing the variation of absorption coefficient with frequency in the region of an absorption "peak". Where the intensity of the microwave radiation does not exceed the power saturation limit, the area under the peak is directly proportional to the absolute concentration of the gas or constituent. The area of the curve is determined by independently varying the parameters of the spectrometer. The principle parameters are:

(a) the centre frequency of the absorption peak;
(b) the resonant frequency of the chamber gas cell (here the term "chamber" should be construed broadly as including a non-resonant gas chamber coupled to a tunable microwave bandpass transmission filter, wherein the "resonant frequency" corresponds to the centre frequency of the filter), and (c) the source frequency.

In another embodiment, the spectrometer may include in addition to the microwave source, a separate pumping source which injects further energy into the gas or constituent so that higher quantisation levels apply. In this type of spectrometer the amplitude and/or frequency of the signal emitted from the pumping source may be varied to provide double resonant modulation.

Figure 10:
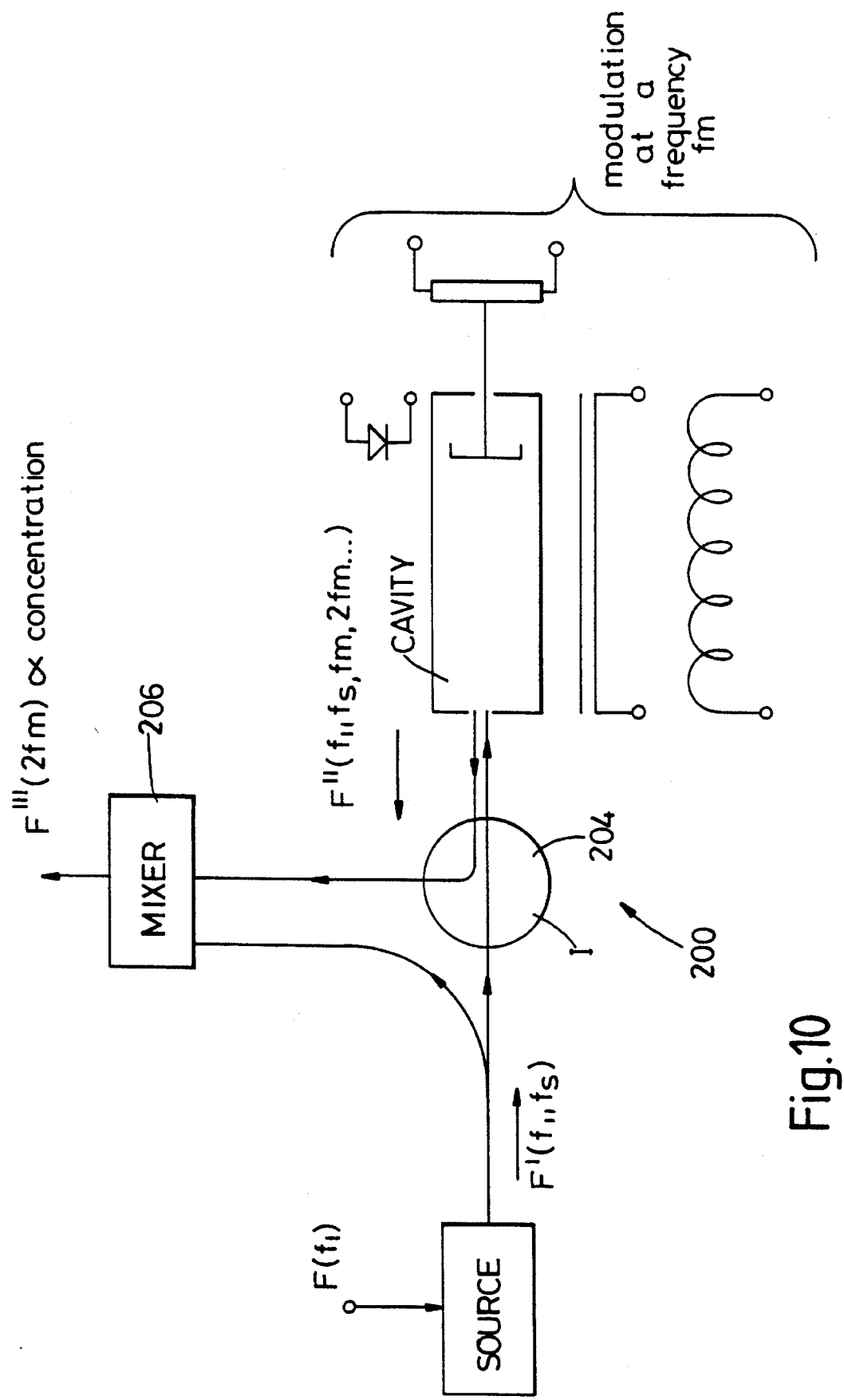
FIG. 10 is a diagram illustrating components of a signal treatment system for the embodiments of FIGS. 1 and 2 which employs superheterodyne demodulation.

In another preferred embodiment, the amplitude modulated signal may be demodulated using a superheterodyne system. This is a general demodulation technique, however, one approach which is believed to be particularly suited to independent or asynchronous scanning is illustrated in FIG. 10. Briefly, the diagram shows a microwave cavity 200 with a microwave source 201, a gas sensing cavity 202, a circulator 204 and a mixer (M). The source frequency $f_s$ is modulated by a signal $F(f_1)$ such that the output from the source is $F'(f_1, f_s)$. This signal is then incident upon the cavity. As a result of the modulation frequency, $f_m$, applied either to the resonant frequency of the cavity or to the centre frequency of the absorption peak (utilizing, say, the Stark or Zeeman effect), the output from the cavity comprises a complex AM signal, $F''$ ($f_1, f_s, f_m, 2f_m$ etc.). By "mixing" the output from the cavity with the original source signal, $F'(f_1, f_s)$ at a mixer 206, it is possible to extract a signal $F'''(2f_m)$ which is directly proportional to the area under the absorption peak and thus to the absolute gas concentration.

In order to avoid problems that may arise such as cost, frequency dependent, fragility etc., it is possible to replace the circulator 204, shown in FIG. 10, with a "transmission" cavity i.e. where the input and output signals do not pass through the same orifice.

Figure 11:
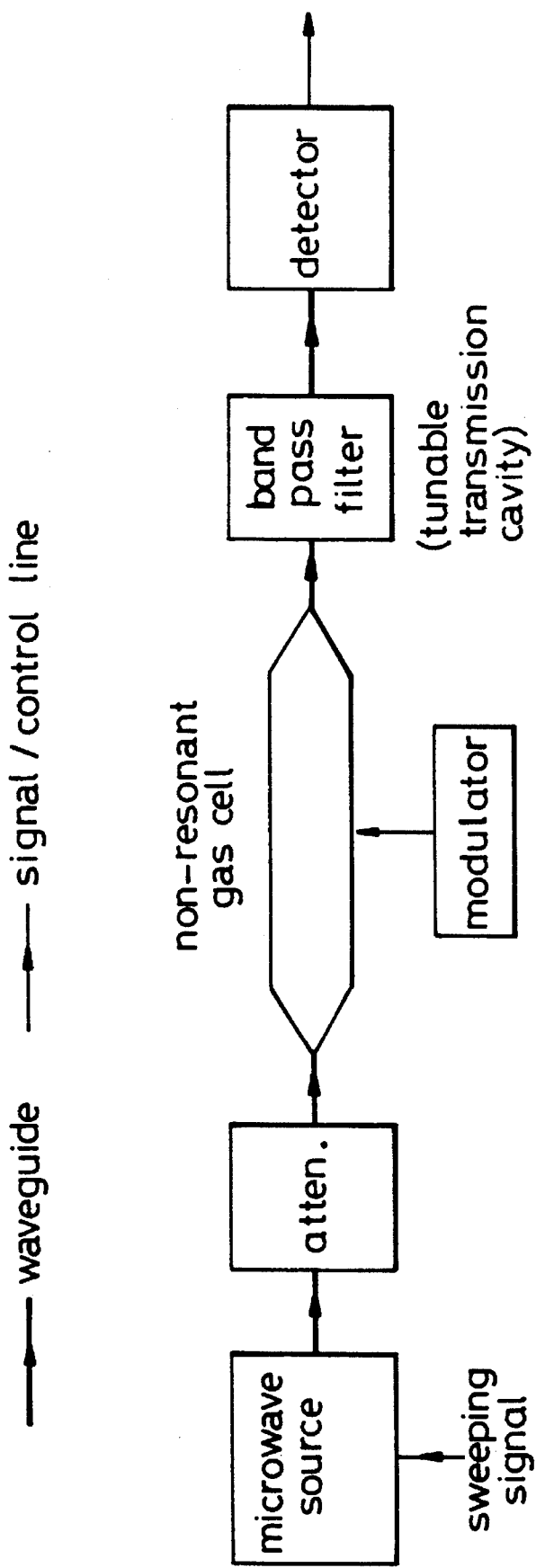
FIG. 11 is a diagram of a signal treatment system with a non-resonant cell in combination with a band pass filter, to exhibit frequency response characteristics analogous to those of a resonant cavity.

Also to avoid the problems associated with using a resonant cavity, a non-resonant cavity coupled to a microwave bandpass filter may be employed as a gas cell as illustrated in FIG. 11. Briefly, a microwave source 210 feeds a microwave beam into a non-resonant gas cell 212 via an attenuator 214. At the outlet end of the gas cell 212 is coupled a bandpass filter 216, the output of the combination being detected by a detector 218. The bandpass filter 216 comprises a tunable transmission cavity which has a similar characteristic to that of a resonant cavity gas cell. The centre frequency of the bandpass filter 216 is used to specify the operating frequency of the gas cell 212 to which it is coupled and as such is analogous to the resonant frequency of a cavity gas cell. As the source frequency 210 is swept across the centre frequency of the bandpass filter 216 a "carrier" signal is generated as a result of amplitude modulation by the resonant characteristics of the bandpass filter 216. This carrier signal then conveys the relevant information arising out of the Stark, Zeeman or double resonance modulation that is applied to the non-resonant gas cell via the appropriate modulator 220.

The techniques described so far rely on the analyte gas or constituent exhibiting a dipole moment, and conventional spectrometers are limited to measuring polar gas molecules. Associated with every molecule there are a number of axes of rotation about which a molecule will exhibit a moment of inertia. The magnitude of these moments of inertia combined with the nature of the quantum mechanical transitions determine the frequencies at which microwave radiation is absorbed. The magnitude of an absorption peak for a given transition is determined by two factors, namely, the dipole moment of the analyte molecules with respect to the principal axes of rotation and the molecular concentration.

For those gas molecules that exhibit a permanent dipole moment such as water vapour, CO, NO, $NO_2$, $N_2O$, $H_2S$ and $SO_2$, it is relatively straightforward to measure molecular concentration using microwave spectroscopy, but many molecules do not exhibit a permanent dipole moment such as carbon dioxide and methane and so the conventional techniques cannot measure such gases. However, our work suggests that a significantly large dipole moment may be induced by applying much less intense fields combined with additional electromagnetic radiation in, for example, the infra red or ultra violet ranges, thus, making microwave spectrometry for non-polar molecules a practical proposition.

It is already known that exposure with infra red, visible light and ultra violet radiation will result in elastic displacements in the molecular structure which give rise to momentary dipole moments. Due to the oscillating nature of these momentary dipoles, the net effect over a period of time is zero. However, should an apparently static external electric field be applied simultaneously then this would result in the presence of a net dipole moment for the duration of that applied field. Given that the force required to separate centres of charge is inversely proportional to the square of the distance between those centres, the magnitude of the electric field required to produce the desired net separation is significantly reduced due to the presence of the initial oscillation.

Another possible means of inducing a dipole moment is to mix the analyte gas with a particularly strongly polar molecular species, thus, utilizing localized field effects or even to us ionizing radiation to create a "permanent" dipole moment within the analyte gas molecules.

Furthermore, the embodiments of spectrometer described above may be modified to operate in the power saturation mode, thereby enabling molecular concentrations to be measured independently of any fluctuations in the magnitude of the induced dipole, thus eliminating a possible source of inaccuracy.

Finally, any of these effects may be useful in reducing the overall voltage required to induce the Start effect, thus, making a Stark spectrometer more acceptable in potentially explosive environments.

Figure 12:
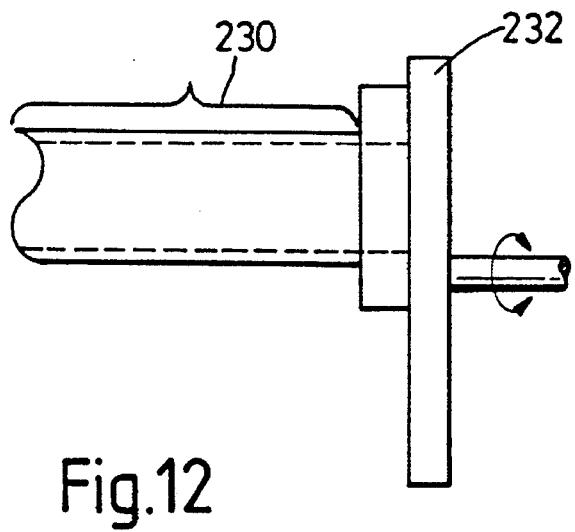
FIG. 12 is a diagram illustrating a rotating sector plate cavity geometry modulator for modulating the geometry of the sensing cavity of a microwave spectrometer in side elevation.
Figure 13:
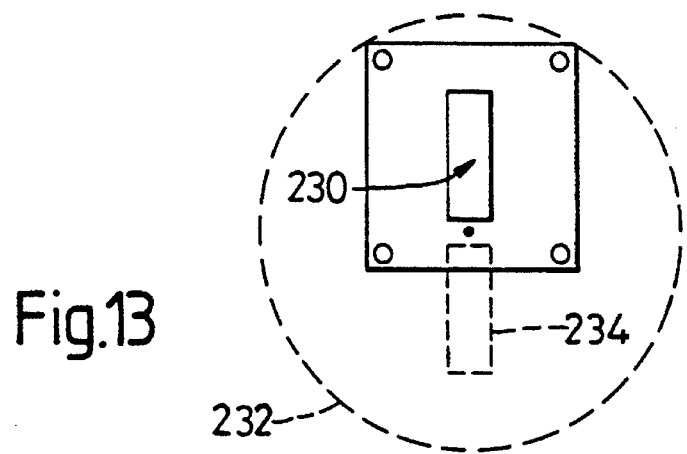
FIG. 13 is a diagram illustrating the modulator of FIG. 12 in end projection.
Figure 14A:
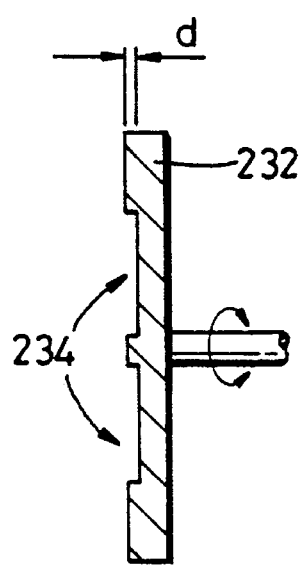
FIGS. 14(a) and 14(b) are diametral section and plan and views respectively of the sector plate.
Figure 14B:
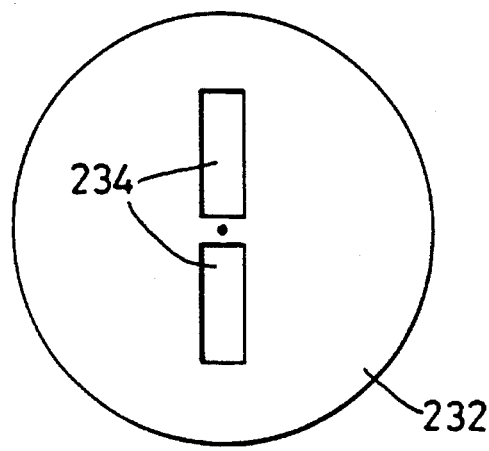

Referring now go FIGS. 12 to 14, the rotating sector plate cavity geometry modulator illustrated there is intended to modulate the resonant frequency of the cavity of a microwave spectrometer, for use in the various embodiments described above.

In microwave spectrometers, the resonant frequency of the cavity may be modulated mechanically or electronically. Mechanical methods rely upon the precise and reproducible variation of one geometric parameter of the cavity, e.g. its length. In the arrangement of FIG. 2, referred to above, a short circuit cavity end wall is formed by the exposed face of a rectangular "piston" closely fitting the internal dimensions of the waveguide/cavity section. The motive force may be provided by any mechanical means but the FIG. 2 arrangement includes a piezoelectric positioning element.

In the arrangement of FIGS. 12 to 14, an end region of the waveguide section 23 is closed by a precision engineered disc or sector plate 232 having machined in the surface facing the waveguide section 230 rectangular concavities 234 matching the cross section of the cavity waveguide lumen and of selected depth "d" such that, as the plate 232 rotates, the effective length of the cavity/waveguide varies precisely by "d". If so desired the gap between the end of the cavity and the disc may be formed as a microwave choke seal to improve the impedance of the interface and thus reduce electromagnetic interference.

We have also developed a further technique which allows a "dither" to component or small displacement component to be applied to the modulation of the resonant cavity. This consists of replacing part of the chamber wall or skinning it with a flexible metallic diaphragm which is displaced micrometricaly by means of an acoustic wave generator such as a piston-phone. Thus the diaphragm may close a chamber which is coupled to a piston-phone by means of a flexible inelastic tube so that the diaphragm may be moved precisely at acoustic frequencies. Where the high displacements or stepping movements are effected by a movable plug member or the like in the chamber in a waveguide part thereof, the diaphragm may be mounted on the face of the plug member facing the chamber.

The spectrometer described herein may be used to detect many different types of gases, but a particular application is measurement of sterilised or other gas or vapour in a sterilising or desorber apparatus. Thus in a further aspect, this invention provides a sterilising apparatus including a sterilising chamber into which items may be introduced for sterilisation, means for sampling the atmosphere within said sterilising chamber, said sampling means including a sensing chamber into which a sample of said chamber atmosphere is introduced, means for propagating microwave radiation in the sensing chamber and means for varying parameters of a resonant cavity by the sensing chamber to adjust the resonant frequency.

In a further aspect, this invention provides a desorbing apparatus, including a desorbing chamber, means for sampling the atmosphere within said desorbing chamber, said sampling means including a sensing chamber into which a sample of said atmosphere is introduced, means for propagating microwave radiation in the sensing chamber and means for varying the sensing chamber to adjust the resonant frequency of said cavity and thereby determine the presence and concentration of gas or vapour in said desorbing chamber.

We claim:

1. Apparatus for detecting at least a concentration of a fluid, comprising:

a chamber into which the fluid is introduced;

propagation means for propagating microwave radiation into said chamber;

microwave modulation means for applying a relatively high frequency modulation to the frequency of said microwave radiation;

further modulation means for applying an independent relatively low frequency modulation to a frequency of a selected absorption peak in the absorption coefficient vs. frequency characteristic of said fluid;

detector means for detecting the microwave radiation reflected from said chamber;

means for selecting a frequency band around said relatively high modulation frequency;

demodulating means for demodulating the output of said detector means within said frequency band with said relatively high modulation frequency; and processor means responsive to the output of said demodulating means and to the variations in said parameters to determine at least said concentration of said fluid.

2. Apparatus according to claim 1, wherein said microwave modulation means applies to said microwave radiation a double frequency modulation comprising a relatively low frequency modulation in addition to said relatively high frequency modulation.

3. Apparatus according to claim 1, wherein said demodulating means includes means for mixing the output of said detector means with a reference signal corresponding to said frequency modulation.

4. Apparatus according to claim 1, wherein said chamber comprises a non-resonant cavity coupled to tuneable transmission filter means, and said detector means detects the radiation transmitted by said filter means.

5. Apparatus according to claim 1, wherein said processing means determines the concentration level of said fluid based upon the area of an absorption peak corresponding to said fluid in the absorption coefficient vs. frequency characteristics thereof.

6. Apparatus according to claim 1, wherein said further modulation means comprises absorption peak frequency modulation means.

7. Apparatus for detecting at least a concentration of a fluid, which comprises:

a chamber into which fluid may be introduced;

microwave generating means for propagating microwave radiation into said chamber;

microwave sweep means for sweeping the frequency of the microwave radiation between preset limits using a relatively high microwave modulation frequency;

further modulation means for applying an independent frequency modulation at a relatively low modulation frequency to the frequency of a selected absorption peak in the absorption coefficient vs. frequency characteristic of said fluid;

detector means for detecting the microwave radiation reflected from said chamber;

first filter means for selecting the signal component from a high frequency band;

first demodulating means for demodulating said selected high frequency component with said relatively high microwave modulating frequency;

second filter means for selecting the signal component from a low frequency band of the output of said detector means corresponding to said relatively low modulation frequency;

second demodulating means for demodulating said selected relatively low frequency component; and processor means responsive to the output of said second demodulating means to determine at least said concentration of said fluid.

* * * * *